US011203747B2

(12) United States Patent
Godawat et al.

(10) Patent No.: US 11,203,747 B2
(45) Date of Patent: Dec. 21, 2021

(54) ELUTION OF BIOMOLECULES FROM MULTI-MODAL RESINS USING MES AND MOPS AS MOBILE PHASE MODIFIERS (71) Applicant: Genzyme Corporation, Cambridge, MA (US)

(72) Inventors: Rahul Godawat, Boylston, MA (US); Daniel Cummings, Framingham, MA (US); Veena Warikoo, Westford, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 16/725,879

(22) Filed: Dec. 23, 2019

(65) Prior Publication Data
US 2020/0131493 A1 Apr. 30, 2020

Related U.S. Application Data (63) Continuation of application No. 14/438,401, filed as application No. PCT/US2013/066319 on Oct. 23, 2013, now abandoned.

(60) Provisional application No. 61/717,880, filed on Oct. 24, 2012.

(51) Int. Cl.
*C12N 9/40* (2006.01)
*B01D 15/38* (2006.01)
*C07K 1/16* (2006.01)
*B01D 15/42* (2006.01)
*A61B 50/00* (2016.01)
*A61B 50/30* (2016.01)
*A61J 1/16* (2006.01)

(52) U.S. Cl.
CPC ............ *C12N 9/2465* (2013.01); *A61B 50/00* (2016.02); *A61B 50/30* (2016.02); *A61J 1/16* (2013.01); *B01D 15/3847* (2013.01); *C07K 1/165* (2013.01); *B01D 15/426* (2013.01); *C12Y 302/01022* (2013.01)

(58) Field of Classification Search
None
See application file for complete search history.

(56) References Cited

U.S. PATENT DOCUMENTS

| 2006/0246544 A1 | 11/2006 | Kang et al. |
| 2011/0160435 A1 | 6/2011 | Borgvall et al. |
| 2011/0166332 A1 | 7/2011 | Gagnon |
| 2011/0178276 A1 | 7/2011 | Cummings et al. |

FOREIGN PATENT DOCUMENTS

| CN | 102066417 | 5/2011 |
| CN | 103201288 | 7/2013 |
| EP | 2 167 526 | 3/2010 |
| EP | 2287174 | 2/2011 |
| MX | 2014/005330 | 9/2014 |
| WO | WO 98/11206 | 3/1998 |
| WO | WO 2009/156430 | 12/2009 |
| WO | WO 2011/049798 | 4/2011 |
| WO | WO 2011/121020 | 10/2011 |
| WO | WO 2011/121031 | 10/2011 |
| WO | WO 2012/059495 | 5/2012 |
| WO | WO 2012/173876 | 12/2012 |
| WO | WO 2013/067301 | 5/2013 |

OTHER PUBLICATIONS

GE HiTrap™ Capto™ IEX Selection Kit Instructions, first published May 2008: 24 pages. (Year: 2008).*
Asenjo, J.A., et al. 2009 J Mol Recognit 22: 65-76. (Year: 2009).*
Arakawa et al., "MEP chromatography of antibody and Fc-fusion protein using aqueous arginine solution," Protein Expression and Purification, 2009, 63:158-163.
Australian Office Action in Patent Application No. 2013334644, dated Jun. 22, 2017, 4 pages.
Australian Office Action in Patent Application No. 2018241214, dated Jun. 12, 2019, 3 pages.
Beck, "Agalsidase alfa, A preparation for, enzyme replacement therapy in Anderson-Fabry disease," Expert Opinion on Investigational Drugs, 2002, 11(6):851-858.
Canadian Office Action in Patent Application No. 2,888,824, dated May 7, 2020, 3 pages.
Charoenrat et al., "Recovery of recombinant β-glucosidase by expanded bed adsorption from Pichia pastoris high-cell-density culture broth," Journal of Biotechnology, 122:86-98 (2006).
Chinese Office Action in Patent Application No. 201380067814.0, dated Apr. 18, 2016, 16 pages.
Chinese Office Action in Patent Application No. 201380067814.0, dated Sep. 14, 2017, 3 pages.
Chinese Office Action in Patent Application No. 201380067814.0, dated Mar. 9, 2018, 8 pages.
Chinese Office Action in Patent Application No. 201610146521.7, dated May 28, 2019, 10 pages.
Chinese Office Action in Patent Application No. 201610146521.7, dated Nov. 14, 2018, 19 pages.
Chinese Office Action in Patent Application No. 201380067814.0, dated Jan. 22, 2017, 28 pages.
Chinese Office Action in Patent Application No. 201610146521.7, dated Sep. 30, 2019, 13 pages.
Gagnon et al., "Minibodies and Multimodal Chromatography Methods: A Convergence of Challenge and Opportunity," Bioprocess Int., 2010, vol. 8(2), pp. 26-35.
Holstein et al., "Mobile phase modifier effects in multimodal cation exchange chromatography," Biotchnol. Bioeng., Jan. 2012, 109(1): 176-186.

(Continued)

Primary Examiner — Marsha Tsay
(74) Attorney, Agent, or Firm — Fish & Richardson P.C.

(57) ABSTRACT

The present invention relates to methods for purifying or enriching a biomolecule using multimodal resins and an elution buffer containing a Good's buffer.

14 Claims, 6 Drawing Sheets (56) References Cited

OTHER PUBLICATIONS

International Preliminary Report on Patentability in International Application No. PCT/US2012/066319, dated Apr. 28, 2015, 8 pages.
International Search Report and Written Opinion in International Application No. PCT/US2013,066319, dated Jan. 23, 2014, 11 pages.
Kaleas et al., "Industrial case study: evaluation of a mixed-mode resin for selective capture of a human growth factor recombinantly expressed in E. coli," J. Chromatogr A, Jan. 2010, 1217(2):235-242.
Merck Biological Buffer Substances, Jul. 2005, 24 pages 2005.
Mexican Office Action in Patent Application No. MX/a/2015/005313, dated Feb. 5, 2019.
Mexican Office Action in Patent Application No. MX/a/2015/005313, dated Aug. 14, 2019, 3 pages.
Mexican Office Action in Patent Application No. MX/a/2015/005313, dated Feb. 13, 2020, 5 pages.
Sigma MOPS product information 2003: 2 pages (2003).
Singapore Written Opinion in Patent Application No. 11201502918R, dated Dec. 5, 2016, 8 pages.
Singapore Written Opinion in Patent Application No. 11201502918R, dated Feb. 19, 2018, 7 pages.
Speka et al., "Purification and Properties of a Thermoactive Glucoamyase from Clostridium thermosaccharolyticum," Applied and Environmental Microbiology, 1991, 57:2317-2323.
European Communication in Patent Application No. 13789418.4, dated May 12, 2020, 2 pages.
Canadian Office Action in Patent Application No. 2,888,824, dated Dec. 2, 2019, 3 pages.
Chinese Office Action in Patent Application No. 201380067814.0, dated Dec. 2, 2020, 16 pages.
European Communication in Patent Application No. 13789418.4, dated Sep. 20, 2018, 5 pages.
Indian Office Action in Patent Application No. 1369/KOLNP/2015, dated Jul. 16, 2018, 8 pages.
Mexican Office Action in Patent Application No. MX/a/2015/005313, dated Nov. 24, 2020, 6 pages.

* cited by examiner

ELUTION OF BIOMOLECULES FROM MULTI-MODAL RESINS USING MES AND MOPS AS MOBILE PHASE MODIFIERS

CROSS-REFERENCE TO RELATED APPLICATIONS

This application is a continuation of U.S. application Ser. No. 14/438,401, filed Apr. 24, 2015, which is a 371 National Phase Entry application of co-pending International Application No. PCT/US2013/066319, filed Oct. 23, 2013, which claims the benefit under 35 U.S.C. § 119 of U.S. Provisional Application 61/717,880, filed Oct. 24, 2012, all of which are hereby incorporated by reference in their entirety.

FIELD OF THE INVENTION

The present invention relates to methods for purifying or enriching a biomolecule using multimodal resins and an elution buffer containing a Good's buffer.

BACKGROUND OF THE INVENTION

Multimodal resins (also termed mixed mode resins) are chromatography media that contain at least two different groups that interact with the target molecule by at least two different mechanisms. For example, multimodal ion exchangers carry a charged group (e.g., a positively charged amino group, a positively charged quarternary ammonium group; a negatively charged carboxylic acid group, a negatively charged sulfonic acid group) which may interact by charge-charge interactions with the target molecule. These multimodal ion exchangers additionally carry another group that may interact with the target molecule by different modes of action, such as hydrophobic interactions, van der Waals interactions, dipole interactions, cation-pi interactions, or hydrogen bonding.

EP 2 167 526 B1 describes the purification of coagulation Factor VIII using a multimodal resin containing ligands which comprise a hydrophobic part and a negatively charged part. The elution is carried out with an elution buffer containing a high concentration of salt (>1.5 M), at least 40% (w/v) ethylene glycol, propylene glycol, or a mixture thereof, and calcium ions.

US 2011/0160435 A1 describes another process for the purification of coagulation factor VIII using a multimodal resin. The elution buffer comprises at least one amino acid that is positively charged at pH 6 to 8. Preferably, the amino acid is selected from lysine, arginine and histidine and is used in concentrations above 0.4 M, especially above 0.5 M.

US 2011/0166332 A1 describes a method for separating at least one non-aggregated protein from a liquid protein preparation by contacting said preparation with a multimodal anion exchanger. The experimental section describes the separation of non-aggregated IgG using an elution buffer containing 1 M glycine in 20 mM Tris, 20 mM Hepes, 20 mM MES, 50 mM NaCl with a linear gradient from pH 9.0 to pH 4.5.

SUMMARY OF THE INVENTION

In a first aspect the present invention relates to a method for purifying or enriching a biomolecule, said method comprising the steps:
(a) providing an aqueous solution containing said biomolecule;
(b) contacting said aqueous solution with a multimodal resin;
(c) optionally washing the multimodal resin with an aqueous washing buffer;
(d) eluting the biomolecule from the multimodal resin with an aqueous buffer solution, wherein said aqueous buffer solution comprises, essentially consists of or consists of: at least 15 mM at least one Good's buffer; between 0 and 400 mM in total concentration of one or more of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; between 0 and 400 mM in total concentration of one or more of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) of ethylene glycol or propylene glycol or a mixture of ethylene glycol and propylene glycol; and
(e) collecting biomolecule containing fractions, thereby obtaining the biomolecule in purified or enriched form.

In one embodiment, the aqueous buffer solution comprises 15 mM to 2.5 mM Good's buffer, such as at least 20 mM, 50 mM, 100 mM, 150 mM, 200 mM or more of a Good's buffer. In another embodiment, the aqueous buffer comprises between 10 mM and 400 mM of one or more of alanine, asparagine, aspartic acid, cysteine, glutamine, glycine, histidine, isoleucine, leucine, lysine, methionine, phenylalanine, proline, serine, threonine, tryptophan, tyrosine, and valine; between 10 mM and 400 mM of one or more of guanidinium thiocyanate, ammonium chloride, ammonium sulfate, ammonium phosphate, ammonium acetate, sodium chloride, sodium citrate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 1% and 60% (v/v) of ethylene glycol or propylene glycol or a mixture of ethylene glycol and propylene glycol.

In one embodiment, the Good's buffer in the aqueous buffer is MES, MOPS or Tris.

In a second aspect, the invention relates to a purified biomolecule, such as a protein, obtainable by the method according to the first aspect.

In a third aspect the present invention relates to a preparation comprising:
(a) a biomolecule; and
(b) an aqueous buffer solution comprising, essentially consisting of or consisting of at least 15 mM of at least one Good's buffer; between 0 and 400 mM in total concentration of one or more of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; between 0 and 400 mM in total concentration of one or more of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) of ethylene glycol or propylene glycol or a mixture of ethylene glycol and propylene glycol.

In one embodiment, the aqueous buffer solution comprises 15 mM to 2.5 mM of a Good's buffer, such as at least 20 mM, 50 mM, 100 mM, 150 mM, 200 mM or more of a Good's buffer. In another embodiment, the aqueous buffer comprises between 10 mM and 400 mM of one or more of alanine, asparagine, aspartic acid, cysteine, glutamine, glycine, histidine, isoleucine, leucine, lysine, methionine, phenylalanine, proline, serine, threonine, tryptophan, tyrosine, and valine; between 10 mM and 400 mM of one or more of guanidinium thiocyanate, ammonium chloride, ammonium sulfate, ammonium phosphate, ammonium acetate, sodium chloride, sodium citrate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 1% and 60% (v/v) of ethylene glycol or propylene glycol or a mixture of ethylene glycol and propylene glycol.

In one embodiment, the Good's buffer in the aqueous buffer is MES, MOPS or Tris.

In a fourth aspect, the invention relates to a use of an aqueous buffer solution for desorbing a biomolecule from a multimodal resin, wherein said aqueous buffer solution comprises, essentially consists of or consists of at least 15 mM of at least one Good's buffer; between 0 and 400 mM in total concentration of one or more of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; between 0 and 400 mM in total concentration of one or more of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) of ethylene glycol or propylene glycol or a mixture of ethylene glycol and propylene glycol.

For example, in certain embodiments, the aqueous buffer solution comprises 15 mM to 2.5 mM of a Good's buffer, such as at least 20 mM, 50 mM, 100 mM, 150 mM, 200 mM or more of a Good's buffer. In another embodiment, the aqueous buffer comprises between 10 mM and 400 mM of one or more of alanine, asparagine, aspartic acid, cysteine, glutamine, glycine, histidine, isoleucine, leucine, lysine, methionine, phenylalanine, proline, serine, threonine, tryptophan, tyrosine, and valine; between 10 mM and 400 mM of one or more of guanidinium thiocyanate, ammonium chloride, ammonium sulfate, ammonium phosphate, ammonium acetate, sodium chloride, sodium citrate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 1% and 60% (v/v) of ethylene glycol or propylene glycol or a mixture of ethylene glycol and propylene glycol.

In one embodiment, the Good's buffer in the aqueous buffer is MES, MOPS or Tris.

In a fifth aspect, the present invention relates to use of an aqueous buffer solution for increasing the recovery rate of a biomolecule adsorbed on a multimodal resin by contacting (a) the multimodal resin onto which said biomolecule has been adsorbed with (b) the aqueous buffer solution, wherein the aqueous buffer solution comprises, essentially consists of or consists of at least 15 mM of at least one Good's buffer; between 0 and 400 mM in total concentration of one or more of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine; between 0 and 400 mM in total concentration of one or more of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) of ethylene glycol or propylene glycol or a mixture of ethylene glycol and propylene glycol.

For example, the aqueous buffer solution for increasing the recovery rate of a biomolecule adsorbed on a multimodal resin can include at least 15 mM, at least 100 mM, or at least 200 mM of a Good's buffer; between 10 mM and 400 mM of one or more of alanine, asparagine, aspartic acid, cysteine, glutamine, glycine, histidine, isoleucine, leucine, lysine, methionine, phenylalanine, proline, serine, threonine, tryptophan, tyrosine, and valine; between 10 mM and 400 mM of one or more of guanidinium thiocyanate, ammonium chloride, ammonium sulfate, ammonium phosphate, ammonium acetate, sodium chloride, sodium citrate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 1% and 60% (v/v) of ethylene glycol or propylene glycol or a mixture of ethylene glycol and propylene glycol.

In one embodiment, the solution comprising the biomolecule recovered from the multimodal resin is applied to one or more of ultrafiltration/diafiltration (UF/DF), tangential flow filtration (TFF), microfiltration (MF) and hydrophobic interaction chromatography (HIC). In one embodiment, the solution comprising the biomolecule recovered from the multimodal resin is applied to HIC.

In a sixth aspect, the present invention relates to an article of manufacture comprising:
(a) a packaging material or container;
(b) an aqueous buffer solution comprising, essentially consisting of or consisting of:
  at least 15 mM of at least one Good's buffer;
  between 0 and 400 mM in total concentration of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;
  between 0 and 400 mM in total concentration of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) of ethylene glycol or propylene glycol or a mixture of ethylene glycol and propylene glycol;

and (c) a data carrier containing instructions for carrying out a method according to the first aspect.

In one embodiment, the aqueous buffer solution in the article of manufacture includes at least 15 mM, at least 100 mM, or at least 200 mM of a Good's buffer; between 10 mM and 400 mM of one or more of alanine, asparagine, aspartic acid, cysteine, glutamine, glycine, histidine, isoleucine, leucine, lysine, methionine, phenylalanine, proline, serine, threonine, tryptophan, tyrosine, and valine; between 10 mM and 400 mM of one or more of guanidinium thiocyanate, ammonium chloride, ammonium sulfate, ammonium phosphate, ammonium acetate, sodium chloride, sodium citrate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 1% and 60% (v/v) of ethylene glycol or propylene glycol or a mixture of ethylene glycol and propylene glycol.

Other features and advantages will be apparent from the accompanying drawings and description, and from the claims.

BRIEF DESCRIPTION OF THE DRAWINGS

FIGS. 6A-C are the multimodal ligands of Pall PPA HyperCel™, Pall HEA HyperCel™, and Pall MEP HyperCel™.

DETAILED DESCRIPTION OF THE INVENTION

The invention is based on the discovery that both MES and MOPS, which are typically used as buffering agents, are surprisingly effective in disrupting multimodal interactions. Thus, by using MES, MOPS or other Good's buffers, it is possible to lower the concentration of arginine or related mobile phase modifiers with high conductivity or to use elution buffers free, or substantially free, from arginine and related mobile phase modifiers when desorbing biomolecules from multimodal chromatographic resins. Furthermore, by using an increased concentration of MES, MOPS or other Good's buffers in accordance with the present invention, it is possible to significantly reduce or even completely avoid the presence of chaotropic agents in the elution buffer.

Desorption of biomolecules bound to a multimodal chromatographic resin can be challenging due to the complex nature of interactions that combine ionic, hydrogen bonding and hydrophobic interactions. Traditional mobile phase additives, such as simple salts (e.g., NaCl) and organic solvents, may not work well for desorption of biomolecules due to opposing effects on individual modes of interaction. For example, addition of NaCl weakens ionic interactions but strengthens hydrophobic interactions and, vice versa for organic solvents. Therefore, special mobile phase modifiers are needed to disrupt multimodal interactions collectively. Use of arginine, guanidine, urea and sodium caprylate have been reported in the literature (Arakawa et al, Protein Expression and Purification 63 2009 pp. 158-163, Kaleas et al, J. Chromatogr. A, 1217, 2010 pp. 235-242 and Holstein et al, Biotechnol. Bioeng., 19 Jan. 2012).

Solutions of the above-mentioned mobile phase modifiers (e.g., arginine or other amino acids) typically exhibit a high conductivity, which is disadvantageous for subsequent purification steps (e.g., ion exchange steps) that are often carried out after the multimodal resin chromatography. More specifically, a high conductivity may require large dilutions or extended times of dialysis. Furthermore, several of the commonly used mobile phase modifiers can denature the quaternary structure or even the tertiary structure of biomolecules (e.g., proteins), if such mobile phase modifiers are present in high concentration. The risk of denaturation is particularly high if the mobile phase modifier is a chaotropic agent, such as urea or a guanidinium salt.

Therefore, it would be desirable to reduce the concentration of arginine or other additives with high conductivity and to identify mobile phase modifiers that exhibit low conductivity. It is further desirable to reduce the concentration of chaotropic agents (such as urea, gunadinium chloride, guanidinium thiocyanate) in the elution buffer and to identify mobile phase modifiers that exert a weak effect, or have no denaturing effect, on biomolecules.

Definitions

The present invention is not limited to the particular methodology, protocols and reagents described herein as these may vary. Further, the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

The terms used herein are defined as described in "A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims that follow, unless the context requires otherwise, the word "comprise,"

and variations such as "comprises" and "comprising," will be understood to imply the inclusion of a stated integer or step or group of integers or steps but not the exclusion of any other integer or step or group of integer or step.

Several documents (for example: patents, patent applications, scientific publications, manufacturers specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

The term "Good's buffer" originally referred to one of twelve buffering agents that were selected and described by Norman Good and colleagues in 1966 as particularly suitable for biological research. In the context of the present specification, the "Good's buffer" does not only encompass the originally described twelve buffering agents but further encompasses structurally related buffering agents. Accordingly, as used herein, the term "Good's buffer" comprises the following chemical compounds: ADA, ACES, BES, Bicine, CAPS, CAPSO, CHES, HEPES, MES, MOPS, PIPES, TAPS, TES, and Tris.

ADA is an abbreviation for N-(2-Acetamido)iminodiacetic acid.

ACES is an abbreviation for N-(2-Acetamido)-2-aminoethanesulfonic acid.

BES is an abbreviation for N,N-Bis(2-hydroxyethyl)-2-aminoethanesulfonic.

Bicine is an abbreviation for N,N-Bis(2-hydroxyethyl) glycine

CAPS is an abbreviation for 3-(Cyclohexylamino)-1-propanesulfonic acid.

CAPSO is an abbreviation for 3-(Cyclohexylamino)-2-hydroxy-1-propanesulfonic acid.

CHES is an abbreviation for 2-(Cyclohexylamino)ethanesulfonic acid.

HEPES is an abbreviation for 4-(2-Hydroxyethyl)piperazine-1-ethanesulfonic acid.

MES is an abbreviation for 2-(N-Morpholino)ethanesulfonic acid.

MOPS is an abbreviation for 3-(N-Morpholino)propanesulfonic acid.

PIPES is an abbreviation for 1,4-Piperazinediethanesulfonic acid.

TAPS is an abbreviation for N-[Tris(hydroxymethyl)methyl]-3-aminopropanesulfonic acid.

TES is an abbreviation for 2-[(2-Hydroxy-1,1-bis(hydroxymethyl)ethyl)amino]ethane-sulfonic acid.

Tris is an abbreviation for Tris(hydroxymethyl)aminomethane.

Figure 6A:
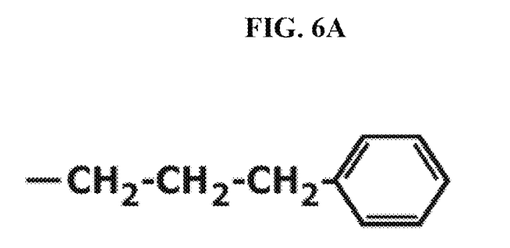
FIG. 6A shows the phenylpropyl substituent of Pall PPA HyperCel™, which is bound to an amine group (not shown).
Figure 6B:
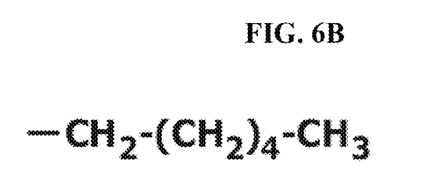
FIG. 6B shows the n-hexyl substituent of Pall HEA HyperCel™, which is bound to an amine group (not shown).
Figure 6C:
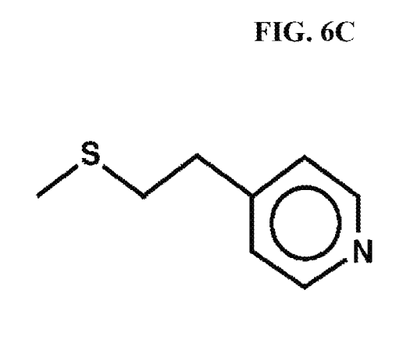
FIG. 6C shows the 4-mercapto-ethyl-pyridine ligand of Pall MEP HyperCel™.

Pall MEP HyperCel™ is a chromatography sorbent composed of a rigid cellulose matrix to which 4-Mercapto-Ethyl-Pyridine (4-MEP) is linked (see FIG. 6C). The cellulose bead confers high porosity, chemical stability and low non-specific interaction. The average bead diameter is 80 µm to 100 µm. Pall MEP HyperCel™ operates by a mixed-mode or multi-mode mechanism also described as Hydrophobic Charge Induction Chromatography (HCIC). HCIC is based on the pH-dependent behavior of ionizable, dual-mode ligands.

Pall PPA HyperCel™ is a chromatography mixed-mode sorbent. The sorbent material is based on high porosity crossed-linked cellulose and contains phenylpropylamine groups as ligands (see FIG. 6A).

Pall HEA HyperCel™ is a chromatography mixed-mode sorbent. The sorbent material is based on high porosity crossed-linked cellulose and contains hexylamine groups as ligands (see FIG. 6B).

Figure 4:
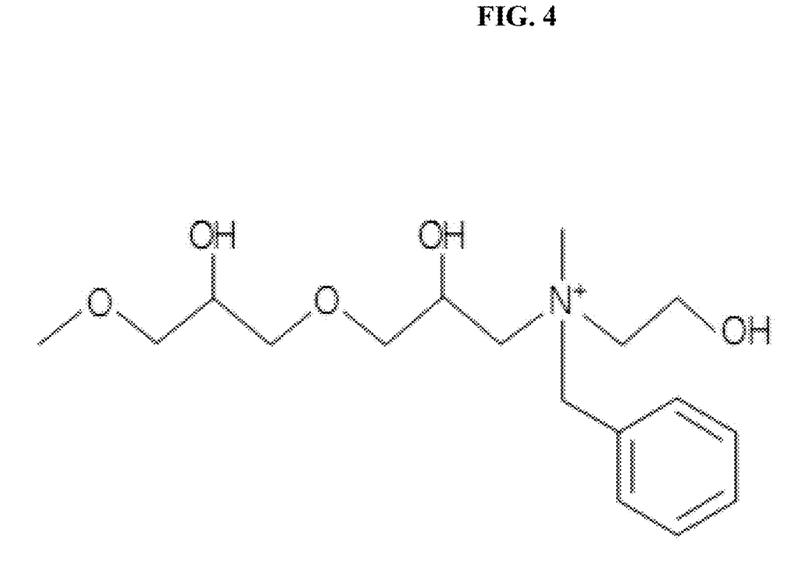
FIG. 4 is the multimodal ligand of Capto™ Adhere. The leftmost part of the molecule forms the linkage to the support matrix.

Capto™ Adhere is a chromatography sorbent employing the ligand N-benzyl-N-methyl-ethanolamine immobilized on porous agarose particles. It is obtainable from GE Healthcare Life Sciences. The detailed chemical structure of this ligand is shown in FIG. 4.

Figure 5:
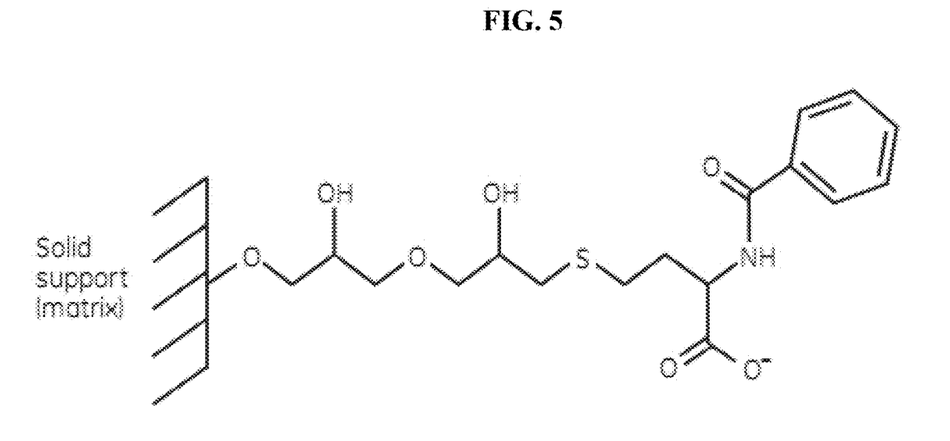
FIG. 5 is the multimodal ligand of Capto™ MMC.

Capto™ MMC is a chromatography sorbent employing a ligand derived from N-benzoyl-methionine immobilized on porous agarose particles. It is obtainable from GE Healthcare Life Sciences. The detailed chemical structure of this ligand is shown in FIG. 5.

Figure 7:
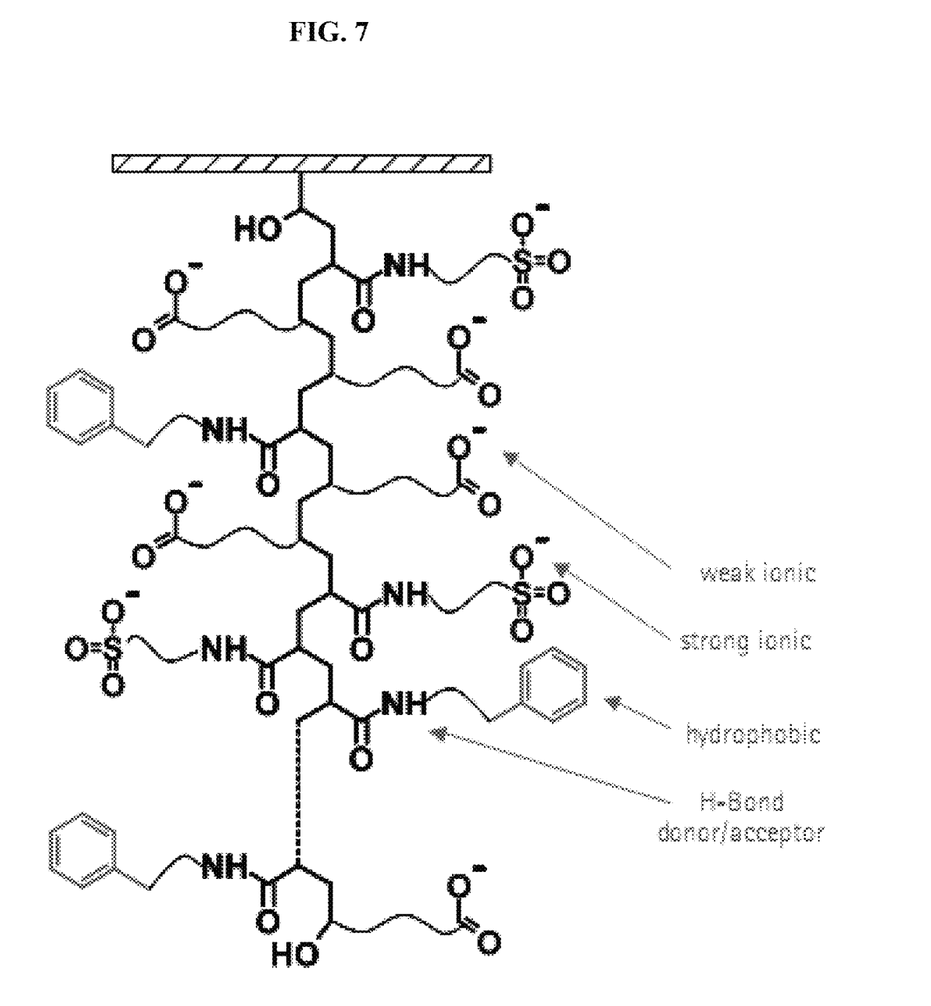
FIG. 7 is the multimodal ligand of Eshmuno® HCX resin obtainable from Merck Millipore, Germany.

Eshmuno® HCX media is a mixed-mode resin that couples a tentacle structure (of the ligands) with a hydrophilic polyvinyl ether base matrix. More specifically, the base matrix is a surface grafted rigid polyvinyl ether hydrophilic polymer. The mean particle size ($d_{50}$) is 75 µm to 95 µm. The detailed chemical structure of the ligand employed in Eshmuno® HCX media is shown in FIG. 7. The Eshmuno® HCX media is obtainable from Merck Millipore, Germany, or EMD Millipore, USA.

Alpha-Galactosidase

Alpha-galactosidase is a glycoside hydrolase enzyme that hydrolyses the terminal alpha-galactosyl moieties from glycolipids and glycoproteins. It is encoded by the GLA gene. This enzyme is a homodimeric glycoprotein that hydrolyses the terminal alpha-galactosyl moieties from glycolipids and glycoproteins. It predominantly hydrolyzes ceramide trihexoside, and it can catalyze the hydrolysis of melibiose into galactose and glucose.

A variety of mutations in this gene affect the synthesis, processing, and stability of this enzyme, which causes Fabrys disease, a rare lysosomal storage disorder and sphingolipidosis that results from a failure to catabolize alpha-D-galactosyl glycolipid moieties. Two enzyme replacement therapies are available to functionally compensate for alpha-galactosidase deficiency. Agalsidase alpha and beta are both recombinant forms of the human α-galactosidase A enzyme and both have the same amino acid sequence as the native enzyme. Agalsidase alpha and beta differ in the structures of their oligosaccharide side chains. The pharmaceutical company Shire manufactures agalsidase alpha under the brand name Replegal® as a treatment for Fabry's disease. The pharmaceutical company Genzyme produces synthetic agalsidase beta under the brand name Fabrazyme® for treatment of Fabry's disease.

Each of the below aspects may be combined with any other aspect or aspects unless clearly indicated to the contrary. In particular, any feature indicated as being preferred or advantageous may be combined with any other feature or features indicated as being preferred or advantageous, unless clearly indicated to the contrary. The present invention is especially directed to those embodiments, in which particularly preferred features are combined with one or more other particularly preferred features.

In a first aspect the present invention is directed to a method for purifying or enriching a biomolecule, said method comprising the steps:

(a) providing an aqueous solution containing the biomolecule;

(b) contacting the aqueous solution with a multimodal resin;

(c) optionally washing the multimodal resin with an aqueous washing buffer;

(d) eluting the biomolecule from the multimodal resin by an aqueous buffer solution,
wherein the aqueous buffer solution comprises, essentially consists of or consists of:
- at least 15 mM of at least one Good's buffer, such as between 15 mM and 2.5 M of at least one Good's buffer, between 50 mM and 2.0 M, between 75 mM and 1.5 M, between 100 mM and 1.25 M, between 200 mM and 1.0 M, between 300 mM and 900 mM, or between 400 mM and 750 mM of at least one Good's buffer;
- between 0 and 400 mM (such as 0 mM, between 10 mM and 350 mM, between 25 mM and 300 mM, between 50 mM and 250 mM, between 100 mM and 200 mM or between 125 mM and 150 mM), in total concentration of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;
- between 0 and 400 mM (such as 0 mM, between 10 mM and 350 mM, between 25 mM and 300 mM, between 50 mM and 250 mM, between 100 mM and 200 mM or between 125 mM and 150 mM) in total concentration of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and
- between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol or propylene glycol or a mixture of ethylene glycol and propylene glycol;

and
(e) collecting biomolecule containing fractions, thereby obtaining the biomolecule in purified or enriched form.

The method according to the first aspect provides several advantages as compared to previous methods for purifying or enriching biomolecules. Previous methods of purifying or enriching biomolecules using multimodal chromatography typically employ elution buffers containing either high concentrations of arginine, glycine, or other amino acids (e.g., 1 M glycine, cf. example 1 of US 2011/0166332 A1; or 0.8 mol/kg L-arginine, cf. example 10 of US 2011/0160435 A1) or high concentrations of salt (e.g., up to 2.5 M of $NH_4Cl$ or NaCl, cf. example 6 of EP 2 167 526 B1). However, arginine and other additives exhibit a high conductivity which is disadvantageous in subsequent purification steps (e.g., ion exchange steps) that are often carried out after the multimodal resin chromatography. In particular, a high conductivity may require large dilutions or extended times of dialysis. In addition, high concentrations of salts can denature the quaternary structure or even the tertiary structure of biomolecules (e.g., proteins). The risk of denaturation is particularly high if the salt is a chaotropic agent (e.g., guanidinium salts or lithium perchlorate).

The method according to the first aspect provides the advantage that the desorption of the biomolecule is effected by an elution buffer containing only low concentrations of amino acids (such as between 0 and 400 mM, such as between 10 mM and 300 mM) and only low concentrations of salts or chaotropic agents (such as between 0 and 400 mM, such as between 10 mM and 300 mM), thereby reducing the risk of denaturing the biomolecule and facilitating subsequent purification steps. This advantage is achieved by increasing the concentration of the Good's buffer in the elution buffer to values of at least 15 mM, at least 50 mM, at least 100 mM or at least 200 mM. Good's buffers are well known for their use in biological research and typically have mild to no effects on biomolecules. Accordingly, the purification or enrichment method of the present invention is gentler than methods traditionally employed.

In summary, desorption of a biomolecule, such as a protein, such as an enzyme, is effected in accordance with the invention either by a Good's buffer in a concentration of 15 mM or more (such as 50 mM, 100 mM or 200 mM or more) in combination with an amino acid in a concentration below 400 mM or by a Good's buffer in a concentration of 15 mM or more, such as 50 mM, 100 mM or 200 mM, in combination with ethylene glycol and/or propylene glycol in a total concentration of not more than 60% (v/v). Of course, the amino acid and the glycol may also be present at the same time.

In some embodiments, the aqueous buffer solution contains at least one amino acid (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine), or ethylene glycol or propylene glycol or a mixture of ethylene glycol and propylene glycol. In other words, in these embodiments the concentrations of ethylene glycol and propylene glycol are each 0%, if the aqueous buffer solution contains one or more amino acids. Conversely, in these embodiments the total concentration of said one or more amino acids is 0 mM, if the aqueous buffer solution contains ethylene glycol or propylene glycol or both.

In some embodiments, the aqueous buffer solution comprises between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol.

In those embodiments in which the aqueous buffer solution contains at least one amino acid, the at least one amino acid is typically selected from the group consisting of alanine, asparagine, cysteine, glutamine, glycine, histidine, isoleucine, leucine, lysine, methionine, phenylalanine, proline, serine, threonine, and valine. In other words, in these embodiments aspartic acid, glutamic acid, tryptophan and tyrosine are absent. In those embodiments of the first aspect in which the aqueous buffer solution contains at least one amino acid, the at least one amino acid is selected from the group consisting of alanine, cysteine, glycine, histidine, lysine, proline, serine, threonine, and valine. In other words, in these embodiments, asparagine, aspartic acid, glutamic acid, glutamine, isoleucine, leucine, methionine, phenylalanine, tryptophan and tyrosine are typically absent. In those embodiments of the first aspect in which the aqueous buffer solution contains at least one amino acid, the at least one amino acid is typically selected from the group consisting of alanine, glycine, histidine, and lysine. In other words, in these embodiments, asparagine, aspartic acid, cysteine, glutamic acid, glutamine, isoleucine, leucine, methionine, phenylalanine, proline, serine, threonine, tryptophan, tyrosine and valine are typically absent.

In one embodiment, the at least one Good's buffer is selected from the group consisting of MES, MOPS, Tris, ADA, ACES, BES, Bicine, CAPS, CAPSO, CHES, HEPES, PIPES, TAPS, and TES. In one embodiment, the at least one Good's buffer is MES, and in another embodiment, the at least one Good's buffer is MOPS.

In one embodiment, the biomolecule is a protein (such as an enzyme, a structural protein, a transport protein, a signaling protein, a transmembrane protein, a peptide hormone or an antibody) or a fragment thereof, or a nucleic acid (e.g., a single-stranded oligonucleotide, a double-stranded oligonucleotide, a single-stranded polynucleotide, or a double-stranded polynucleotide). The nucleic acid can be, for example, DNA, RNA or a hybrid double-strand formed from DNA and RNA. In one embodiment, the biomolecule is an enzyme (e.g., an oxidoreductase, a transferase, a hydrolase, a lyase, an isomerase, or a ligase). For example, in one embodiment, the enzyme is a hydrolase, such as a glycosidase (often also termed glycoside hydrolase). In one embodiment, the glycosidase is an alpha-galactosidase, such as an alpha-galactosidase selected from the group consisting of agalsidase alpha (e.g., Replegal® manufactured by Shire, United Kingdom) and agalsidase beta (e.g., Fabrazyme® manufactured by Genzyme, Cambridge, Mass.). In one embodiment, the alpha-galactosidase is agalsidase beta. In another embodiment, the biomolecule is a peptide hormone, such as thyroid-stimulating hormone (also known as TSH or thyrotropin). TSH is a glycoprotein consisting of two subunits: the alpha subunit and the beta subunit. A recombinant form of human TSH-alpha is obtainable from Genzyme Corp. under the tradename "Thyrogen". In yet another embodiment, the biomolecule is an antibody, such as a monoclonal antibody. In certain embodiments, the biomolecule is a glycosylated protein.

In one embodiment of the first aspect, the multimodal resin is selected from the group consisting of Capto™ Adhere, Capto™ MMC, Pall PPA HyperCel™, Pall HEA HyperCel™, Pall MEP HyperCel™, and Eshmuno® HCX media. The ligands used in these multimodal resins on the filing day of the present application are shown in FIGS. 4, 5, 6A, 6B, 6C, and 7. In one embodiment, the multimodal resin is Capto™ Adhere.

In a second aspect, the present invention is directed to a purified biomolecule obtainable or obtained by the method according to the first aspect. A biomolecule can be purified or enriched by a method that is gentler than the purification or enrichment methods typically known in the art. Accordingly, it is expected that the purified biomolecule is in a state that is more native than that of a purified biomolecule obtainable by methods of the prior art.

In some embodiments, the aqueous buffer solution contains either at least one amino acid (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine), or ethylene glycol or propylene glycol or a mixture of ethylene glycol and propylene glycol. In other words, in these embodiments the concentrations of ethylene glycol and propylene glycol are each 0%, if the aqueous buffer solution contains one or more amino acids. Conversely, in these embodiments the total concentration of said one or more amino acids is 0 mM, if the aqueous buffer solution contains ethylene glycol or propylene glycol or both.

In some embodiments, the aqueous buffer solution comprises between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol.

In those embodiments where the aqueous buffer solution contains at least one amino acid, the at least one amino acid is typically selected from the group consisting of alanine, asparagine, cysteine, glutamine, glycine, histidine, isoleucine, leucine, lysine, methionine, phenylalanine, proline, serine, threonine, and valine. In other words, in these embodiments aspartic acid, glutamic acid, tryptophan and tyrosine are typically absent. In those embodiments where the aqueous buffer solution contains at least one amino acid, the at least one amino acid is typically selected from the group consisting of alanine, cysteine, glycine, histidine, lysine, proline, serine, threonine, and valine. In other words, in these embodiments, asparagine, aspartic acid, glutamic acid, glutamine, isoleucine, leucine, methionine, phenylalanine, tryptophan and tyrosine are typically absent. In those embodiments where the aqueous buffer solution contains at least one amino acid, the at least one amino acid is typically selected from the group consisting of alanine, glycine, histidine, and lysine. In other words, in these embodiments, asparagine, aspartic acid, cysteine, glutamic acid, glutamine, isoleucine, leucine, methionine, phenylalanine, proline, serine, threonine, tryptophan, tyrosine and valine are typically absent.

In one embodiment, the at least one Good's buffer is selected from the group consisting of MES, MOPS, Tris, ADA, ACES, BES, Bicine, CAPS, CAPSO, CHES, HEPES, PIPES, TAPS, and TES. In one embodiment, the at least one Good's buffer is MES, and in another embodiment, the at least one Good's buffer is MOPS.

In one embodiment, the biomolecule is a protein (e.g., an enzyme, a structural protein, a transport protein, a signaling protein, a transmembrane protein, a peptide hormone or an antibody) or a fragment thereof, or a nucleic acid (e.g., a single-stranded oligonucleotide, a double-stranded oligonucleotide, a single-stranded polynucleotide, or a double-stranded polynucleotide). The nucleic acid can be, for example, DNA, RNA or a hybrid double-strand formed from DNA and RNA. In one embodiment, the biomolecule is an enzyme (e.g., an oxidoreductase, a transferase, a hydrolase, a lyase, an isomerase, or a ligase). For example, the enzyme can be a hydrolase, such as a glycosidase (often also termed glycoside hydrolase). In one embodiment, the glycosidase is an alpha-galactosidase, such as an alpha-galactosidase selected from the group consisting of agalsidase alpha (e.g., Replegal® manufactured by Shire, United Kingdom) and agalsidase beta (e.g., Fabrazyme® manufactured by Genzyme, Cambridge, Mass.). In one embodiment, the alpha-galactosidase is agalsidase beta. In another embodiment, the biomolecule is a peptide hormone, such as thyroid-stimulating hormone (also known as TSH or thyrotropin). TSH is a glycoprotein consisting of two subunits: the alpha subunit and the beta subunit. A recombinant form of human TSH-alpha is obtainable from Genzyme Corp. under the tradename "Thyrogen." In yet another embodiment, the biomolecule is an antibody, such as a monoclonal antibody. In certain embodiments, the biomolecule is a glycosylated protein.

In one embodiment, the multimodal resin is selected from the group consisting of Capto™ Adhere, Capto™ MMC, Pall PPA HyperCel™, Pall HEA HyperCel™, Pall MEP HyperCel™, and Eshmuno® HCX media. The ligands used in these multimodal resins on the filing day of the present application are shown in FIGS. 4, 5, 6A, 6B, 6C, and 7. In one embodiment, the multimodal resin is Capto™ Adhere.

In a third aspect, the present invention is directed to a preparation comprising:
(a) a biomolecule; and
(b) an aqueous buffer solution comprising, essentially consisting of or consisting of
  at least 15 mM of at least one Good's buffer, such as between 15 mM and 2.5 M of at least one Good's buffer, such as between 50 mM and 2.0 M, between 75 mM and 1.5 M, between 100 mM and 1.25 M, between 200 mM and 1.0 M, between 300 mM and 900 mM, or between 400 mM and 750 mM of at least one Good's buffer;
  between 0 and 400 mM (such as 0 mM, between 10 mM and 350 mM, between 25 mM and 300 mM, between 50 mM and 250 mM, between 100 mM and 200 mM, or between 125 mM and 150 mM), in total concentration of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;
  between 0 and 400 mM (such as 0 mM, between 10 mM and 350 mM, between 25 mM and 300 mM, between 50 mM and 250 mM, between 100 mM and 200 mM, or between 125 mM and 150 mM) in total concentration of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and
  between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol or propylene glycol or a mixture of ethylene glycol and propylene glycol.

As explained above in the section discussing the first aspect, the aqueous buffer solution described herein involves a reduced risk of denaturing a biomolecule as compared to elution buffer solutions described in the art. Therefore, it is expected that the preparation according to the third aspect contains the biomolecule in a state that is more native than that of biomolecules in preparations described in the art.

In some embodiments, the aqueous buffer solution contains either at least one amino acid (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine), or ethylene glycol or propylene glycol or a mixture of ethylene glycol and propylene glycol. In other words, in these embodiments the concentrations of ethylene glycol and propylene glycol are each 0%, if the aqueous buffer solution contains one or more amino acids. Conversely, in these embodiments the total concentration of said one or more amino acids is 0 mM, if the aqueous buffer solution contains ethylene glycol or propylene glycol or both.

In some embodiments, the aqueous buffer solution comprises between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol.

In those embodiments where the aqueous buffer solution contains at least one amino acid, the at least one amino acid is typically selected from the group consisting of alanine, asparagine, cysteine, glutamine, glycine, histidine, isoleucine, leucine, lysine, methionine, phenylalanine, proline, serine, threonine, and valine. In other words, in these embodiments aspartic acid, glutamic acid, tryptophan and tyrosine are typically absent. In those embodiments where the aqueous buffer solution contains at least one amino acid, the at least one amino acid is typically selected from the group consisting of alanine, cysteine, glycine, histidine, lysine, proline, serine, threonine, and valine. In other words, in these embodiments, asparagine, aspartic acid, glutamic acid, glutamine, isoleucine, leucine, methionine, phenylalanine, tryptophan and tyrosine are typically absent. In those embodiments where the aqueous buffer solution contains at least one amino acid, the at least one amino acid is selected from the group consisting of alanine, glycine, histidine, and lysine. In other words, in these embodiments, asparagine, aspartic acid, cysteine, glutamic acid, glutamine, isoleucine, leucine, methionine, phenylalanine, proline, serine, threonine, tryptophan, tyrosine and valine are typically absent.

In one embodiment, the at least one Good's buffer is selected from the group consisting of MES, MOPS, Tris, ADA, ACES, BES, Bicine, CAPS, CAPSO, CHES, HEPES, PIPES, TAPS, and TES. In one embodiment, the at least one Good's buffer is MES, and in another embodiment, the at least one Good's buffer is MOPS.

In one embodiment, the biomolecule is a protein (e.g., an enzyme, a structural protein, a transport protein, a signaling protein, a transmembrane protein, a peptide hormone or an antibody) or a fragment thereof, or a nucleic acid (e.g., a single-stranded oligonucleotide, a double-stranded oligonucleotide, a single-stranded polynucleotide, or a double-stranded polynucleotide). The nucleic acid can be, for example, DNA, RNA or a hybrid double-strand formed from DNA and RNA. In one embodiment, the biomolecule is an enzyme (e.g., an oxidoreductase, a transferase, a hydrolase, a lyase, an isomerase, or a ligase). In one embodiment, the enzyme is a hydrolase, such as a glycosidase (often also termed glycoside hydrolase). In one embodiment, the glycosidase is an alpha-galactosidase, such as an alpha-galactosidase selected from the group consisting of agalsidase alpha (e.g., Replegal® manufactured by Shire, United Kingdom) and agalsidase beta (e.g., Fabrazyme® manufactured by Genzyme, Cambridge, Mass.). In one embodiment, the alpha-galactosidase is agalsidase beta, and in another embodiment, the biomolecule is a peptide hormone, such as thyroid-stimulating hormone (also known as TSH or thyrotropin). TSH is a glycoprotein consisting of two subunits: the alpha subunit and the beta subunit. A recombinant form of human TSH-alpha is obtainable from Genzyme Corp. under the tradename "Thyrogen". In yet another embodiment, the biomolecule is an antibody, such as a monoclonal antibody. In certain embodiments, the biomolecule is a glycosylated protein.

In a fourth aspect, the present invention is directed to a use of an aqueous buffer solution for desorbing a biomolecule from a multimodal resin, wherein said aqueous buffer solution comprises, essentially consists of or consists of:
  at least 15 mM of at least one Good's buffer, such as between 15 mM and 2.5 M of at least one Good's buffer, between 50 mM and 2.0 M, between 75 mM and 1.5 M, between 100 mM and 1.25 M, between 200 mM and 1.0 M, between 300 mM and 900 mM, or between 400 mM and 750 mM of at least one Good's buffer;

between 0 and 400 mM (such as 0 mM, between 10 mM and 350 mM, between 25 mM and 300 mM, between 50 mM and 250 mM, between 100 mM and 200 mM, or between 125 mM and 150 mM), in total concentration of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;

between 0 and 400 mM (such as 0 mM, between 10 mM and 350 mM, between 25 mM and 300 mM, between 50 mM and 250 mM, between 100 mM and 200 mM, or between 125 mM and 150 mM) in total concentration of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol or propylene glycol or a mixture of ethylene glycol and propylene glycol.

As will be illustrated in the experimental section below, the aqueous buffer solution described herein is particularly well suited for desorbing biomolecules from a multimodal resin. It was especially unexpected that Good's buffers could be effective in desorbing biomolecules from a multimodal resin to an extent that is comparable to that of arginine.

In some embodiments, the aqueous buffer solution contains either at least one amino acid (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine), or ethylene glycol or propylene glycol or a mixture of ethylene glycol and propylene glycol. In other words, in these embodiments the concentrations of ethylene glycol and propylene glycol are each 0%, if the aqueous buffer solution contains one or more amino acids. Conversely, in these embodiments the total concentration of said one or more amino acids is 0 mM, if the aqueous buffer solution contains ethylene glycol or propylene glycol or both.

In some embodiments of the fourth aspect, the aqueous buffer solution comprises between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol.

In those embodiments where the aqueous buffer solution contains at least one amino acid, the at least one amino acid is typically selected from the group consisting of alanine, asparagine, cysteine, glutamine, glycine, histidine, isoleucine, leucine, lysine, methionine, phenylalanine, proline, serine, threonine, and valine. In other words, in these embodiments aspartic acid, glutamic acid, tryptophan and tyrosine are typically absent. In those embodiments where the aqueous buffer solution contains at least one amino acid, the at least one amino acid is typically selected from the group consisting of alanine, cysteine, glycine, histidine, lysine, proline, serine, threonine, and valine. In other words, in these embodiments, asparagine, aspartic acid, glutamic acid, glutamine, isoleucine, leucine, methionine, phenylala-nine, tryptophan and tyrosine are typically absent. In those embodiments where the aqueous buffer solution contains at least one amino acid, the at least one amino acid is typically selected from the group consisting of alanine, glycine, histidine, and lysine. In other words, in these embodiments, asparagine, aspartic acid, cysteine, glutamic acid, glutamine, isoleucine, leucine, methionine, phenylalanine, proline, serine, threonine, tryptophan, tyrosine and valine are typically absent.

In one embodiment, the at least one Good's buffer is selected from the group consisting of MES, MOPS, Tris, ADA, ACES, BES, Bicine, CAPS, CAPSO, CHES, HEPES, PIPES, TAPS, and TES. In one embodiment, the at least one Good's buffer is MES, and in another embodiment, the at least one Good's buffer is MOPS.

In one embodiment, the biomolecule is a protein (e.g., an enzyme, a structural protein, a transport protein, a signaling protein, a transmembrane protein, a peptide hormone or an antibody) or a fragment thereof, or a nucleic acid (e.g., a single-stranded oligonucleotide, a double-stranded oligonucleotide, a single-stranded polynucleotide, or a double-stranded polynucleotide). The nucleic acid can be, for example, DNA, RNA or a hybrid double-strand formed from DNA and RNA. In one embodiment, the biomolecule is an enzyme (e.g., an oxidoreductase, a transferase, a hydrolase, a lyase, an isomerase, or a ligase). In one embodiment, the enzyme is a hydrolase, such as a glycosidase (often also termed glycoside hydrolase). In another embodiment, the glycosidase is an alpha-galactosidase, such as agalsidase alpha (e.g., Replegal® manufactured by Shire, United Kingdom) or agalsidase beta (e.g., Fabrazyme® manufactured by Genzyme, Cambridge, Mass.). In one, the alpha-galactosidase is agalsidase beta. In another embodiment, the biomolecule is a peptide hormone, such as thyroid-stimulating hormone (also known as TSH or thyrotropin). TSH is a glycoprotein consisting of two subunits: the alpha subunit and the beta subunit. A recombinant form of human TSH-alpha is obtainable from Genzyme Corp. under the tradename "Thyrogen". In yet another embodiment, the biomolecule is an antibody, such as a monoclonal antibody. In certain embodiments, the biomolecule is a glycosylated protein.

In one embodiment, the multimodal resin is selected from the group consisting of Capto™ Adhere, Capto™ MMC, Pall PPA HyperCel™, Pall HEA HyperCel™, Pall MEP HyperCel™, and Eshmuno® HCX media. The ligands used in these multimodal resins on the filing day of the present application are shown in FIGS. 4, 5, 6A, 6B, 6C, and 7. In one embodiment, the multimodal resin is Capto™ Adhere.

In a fifth aspect, the present invention is directed to a use of an aqueous buffer solution for increasing the recovery rate of a biomolecule adsorbed on a multimodal resin by contacting (a) said multimodal resin onto which said biomolecule has been adsorbed with (b) said aqueous buffer solution, wherein said aqueous buffer solution comprises, essentially consists of or consists of:

at least 15 mM of at least one Good's buffer, such as between 15 mM and 2.5 M of at least one Good's buffer, between 50 mM and 2.0 M, between 75 mM and 1.5 M, between 100 mM and 1.25 M, between 200 mM and 1.0 M, between 300 mM and 900 mM, or between 400 mM and 750 mM of at least one Good's buffer;

between 0 and 400 mM (such as 0 mM, between 10 mM and 350 mM, between 25 mM and 300 mM, between 50 mM and 250 mM, between 100 mM and 200 mM, or between 125 mM and 150 mM), in total concentration of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;

between 0 and 400 mM (such as 0 mM, between 10 mM and 350 mM, between 25 mM and 300 mM, between 50 mM and 250 mM, between 100 mM and 200 mM, or between 125 mM and 150 mM) in total concentration of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol or propylene glycol or a mixture of ethylene glycol and propylene glycol.

As will be illustrated in the experimental section below, the aqueous buffer solution described herein is particularly well-suited for desorbing biomolecules from a multimodal chromatography resin at a high recovery rate. The inventors achieved recovery rates of up to 99% using aqueous buffer solutions featured in the invention (see Table 1).

In some embodiments, the aqueous buffer solution contains either at least one amino acid (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine), or ethylene glycol or propylene glycol or a mixture of ethylene glycol and propylene glycol. In other words, in these embodiments the concentrations of ethylene glycol and propylene glycol are each 0%, if the aqueous buffer solution contains one or more amino acids. Conversely, in these embodiments the total concentration of said one or more amino acids is 0 mM, if the aqueous buffer solution contains ethylene glycol or propylene glycol or both.

In some embodiments of the fifth aspect, the aqueous buffer solution comprises between 0% and 60% (v/v) (such as between 1% and 50% (v/v), between 5% and 40% (v/v), between 8% and 30% (v/v), between 10% and 25% (v/v), or between 15% and 20% (v/v)) of ethylene glycol.

In those embodiments where the aqueous buffer solution contains at least one amino acid, the at least one amino acid is typically selected from the group consisting of alanine, asparagine, cysteine, glutamine, glycine, histidine, isoleucine, leucine, lysine, methionine, phenylalanine, proline, serine, threonine, and valine. In other words, in these embodiments aspartic acid, glutamic acid, tryptophan and tyrosine are typically absent. In those embodiments where the aqueous buffer solution contains at least one amino acid, the at least one amino acid is typically selected from the group consisting of alanine, cysteine, glycine, histidine, lysine, proline, serine, threonine, and valine. In other words, in these embodiments, asparagine, aspartic acid, glutamic acid, glutamine, isoleucine, leucine, methionine, phenylalanine, tryptophan and tyrosine are typically absent. In those embodiments where the aqueous buffer solution contains at least one amino acid, the at least one amino acid is typically selected from the group consisting of alanine, glycine, histidine, and lysine. In other words, in these most embodiments, asparagine, aspartic acid, cysteine, glutamic acid, glutamine, isoleucine, leucine, methionine, phenylalanine, proline, serine, threonine, tryptophan, tyrosine and valine are typically absent.

In one embodiment, the at least one Good's buffer is selected from the group consisting of MES, MOPS, Tris, ADA, ACES, BES, Bicine, CAPS, CAPSO, CHES, HEPES, PIPES, TAPS, and TES. In one embodiment, the at least one Good's buffer is MES, and in another embodiment, the at least one Good's buffer is MOPS.

In one embodiment, the biomolecule is a protein (e.g., an enzyme, a structural protein, a transport protein, a signaling protein, a transmembrane protein, a peptide hormone or an antibody) or a fragment thereof, or a nucleic acid (e.g., a single-stranded oligonucleotide, a double-stranded oligonucleotide, a single-stranded polynucleotide, or a double-stranded polynucleotide). The nucleic acid can be, for example, DNA, RNA or a hybrid double-strand formed from DNA and RNA. In one embodiment, the biomolecule is an enzyme (e.g., an oxidoreductase, a transferase, a hydrolase, a lyase, an isomerase, or a ligase). It another embodiment, the enzyme is a hydrolase, such as a glycosidase (often also termed glycoside hydrolase). In one embodiment, the glycosidase is an alpha-galactosidase, such as an alpha-galactosidase selected from the group consisting of agalsidase alpha (e.g., Replegal® manufactured by Shire, United Kingdom) and agalsidase beta (e.g., Fabrazyme® manufactured by Genzyme, Cambridge, Mass.). In one embodiment, the alpha-galactosidase is agalsidase beta. In another embodiment, the biomolecule is a peptide hormone, such as thyroid-stimulating hormone (also known as TSH or thyrotropin). TSH is a glycoprotein consisting of two subunits: the alpha subunit and the beta subunit. A recombinant form of human TSH-alpha is obtainable from Genzyme Corp. under the tradename "Thyrogen". In yet another embodiment, the biomolecule is an antibody, such as a monoclonal antibody. In other embodiments, the biomolecule is a glycosylated protein.

In one embodiment, the multimodal resin is selected from the group consisting of Capto™ Adhere, Capto™ MMC, Pall PPA HyperCel™, Pall HEA HyperCel™, Pall MEP HyperCel™, and Eshmuno® HCX media. The ligands used in these multimodal resins on the filing day of the present application are shown in FIGS. 4, 5, 6A, 6B, 6C, and 7. In one embodiment, the multimodal resin is Capto™ Adhere.

In a sixth aspect, the present invention is directed to an article of manufacture comprising:
(a) a packaging material or container;
(b) an aqueous buffer solution comprising, essentially consisting of or consisting of:
at least 15 mM of at least one Good's buffer, such as between 15 mM and 2.5 M of at least one Good's buffer, between 50 mM and 2.0 M, between 75 mM and 1.5 M, between 100 mM and 1.25 M, between 200 mM and 1.0 M, between 300 mM and 900 mM, and between 400 mM and 750 mM of at least one Good's buffer;

between 0 and 400 mM (such as 0 mM, between 10 mM and 350 mM, between 25 mM and 300 mM, between 50 mM and 250 mM, between 100 mM and 200 mM, or between 125 and 150 mM), in total concentration of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine;

between 0 and 400 mM (such as 0 mM, between 10 mM and 350 mM, between 25 mM and 300 mM, between 50 mM and 250 mM, between 100 mM and 200 mM, or between 125 and 150 mM) in total concentration of urea, guanidinium chloride, guanidinium thiocyanate, ammonium chloride, ammonium sulfate, ammonium phosphate, ammonium acetate, sodium chloride, sodium citrate, sodium caprylate, sodium phosphate, sodium iodide, potassium chloride, potassium citrate, potassium sulfate, potassium phosphate, potassium iodide, magnesium chloride, magnesium sulfate, magnesium phosphate, calcium chloride, calcium sulfate, calcium phosphate, and taurine; and between 0% and 60% (v/v) (such as between 1% and 50% (v/v), between 5% and 40% (v/v), between 8% and 30% (v/v), between 10% and 25% (v/v), between 15% and 20% (v/v)) of ethylene glycol or propylene glycol or a mixture of ethylene glycol and propylene glycol; and (c) a data carrier containing instructions for carrying out a method described herein.

The aqueous buffer solution featured in the invention involves a reduced risk of denaturing a biomolecule as compared to elution buffer solutions described in the prior art. The article of manufacture according to the sixth aspect provides this advantageous aqueous buffer solution in combination with a container or packaging material and with a data carrier containing instructions for carrying out a method that makes use of this advantageous aqueous buffer solution.

Therefore, it is expected that the preparation according to the present aspect contains the biomolecule in a state that is more native than that of biomolecules in preparations described in the prior art.

In one embodiment, the data carrier is selected from the group consisting of a label present on the packaging material or container (e.g., in the form of an adhesive label, a tag, a chip, or an RFID tag) and a packaging insert (e.g., a leaflet; a booklet; a chip; or a computer-readable storage medium, such as a floppy disk, a CD-ROM, a CD-R, a DVD, or a blue-ray disk). In certain embodiments, the data carrier comprises written information, visual information (e.g., pictures), or computer-readable information (e.g., a program or a bar code).

In one embodiment, the data carrier further comprises one or more of the following information:
(i) instructions for use of aqueous buffer solution;
(ii) quality information such as information about the lot/batch number, the manufacturing or assembly site or the expiry or sell-by date of the aqueous buffer solution; or information concerning the correct storage or handling of the article;
(iii) information concerning the composition of the aqueous buffer solution;
(iv) information concerning the interpretation of information obtained when performing methods according to the first aspect;
(v) a warning concerning possible misinterpretations or wrong results when applying unsuitable methods; and/or
(vi) a warning concerning possible misinterpretations or wrong results when using unsuitable reagent(s) and/or buffer(s).

In one embodiment of the sixth aspect, the article of manufacture further comprises one or more of the following components:
(d) a chromatography medium;
(e) a chromatography column;
(f) a reference biomolecule usable for calibrating a method for purifying or enriching a biomolecule, such as for calibrating a method according to the first aspect.

In some embodiments, the chromatography column is prepacked with the chromatography medium.

In one embodiment, the chromatography medium is a multimodal chromatography resin. The multimodal chromatography resin is typically selected from the group consisting of Capto™ Adhere, Capto™ MMC, Pall PPA HyperCel™, Pall HEA HyperCel™, Pall MEP HyperCel™, and Eshmuno® HCX media. The ligands used in these multimodal resins are shown in FIGS. 4, 5, 6A, 6B, 6C, and 7. In one embodiment, the multimodal resin is Capto™ Adhere.

In one embodiment, the reference biomolecule is selected from the group consisting of a protein (e.g., an enzyme, a structural protein, a transport protein, a signaling protein, a transmembrane protein, a peptide hormone or an antibody) and a nucleic acid (e.g., a single-stranded oligonucleotide, a double-stranded oligonucleotide, a single-stranded polynucleotide, or a double-stranded polynucleotide). The nucleic acid can be DNA, RNA or a hybrid double-strand formed from DNA and RNA. In one embodiment, the reference biomolecule is an enzyme (e.g., an oxidoreductase, a transferase, a hydrolase, a lyase, an isomerase, or a ligase). The reference enzyme can be, for example, a hydrolase, such as a glycosidase (often also termed glycoside hydrolase). In one embodiment, the reference glycosidase is an alpha-galactosidase, such as an agalsidase alpha (e.g., Replagal® manufactured by Shire, United Kingdom) or an agalsidase beta (e.g., Fabrazyme® manufactured by Genzyme, Cambridge, Mass.). In one embodiment, the reference alpha-galactosidase is agalsidase beta. In another embodiment, the reference biomolecule is a peptide hormone, such as thyroid-stimulating hormone (also known as TSH or thyrotropin). TSH is a glycoprotein consisting of two subunits: the alpha subunit and the beta subunit. A recombinant form of human TSH-alpha is obtainable from Genzyme Corp. under the tradename "Thyrogen". In yet another embodiment, the reference biomolecule is an antibody, such as a monoclonal antibody. In certain embodiments, the reference biomolecule is a glycosylated protein.

In some embodiments, the aqueous buffer solution contains either at least one amino acid (e.g., alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine), or ethylene glycol or propylene glycol or a mixture of ethylene glycol and propylene glycol. In other words, in these embodiments the concentrations of ethylene glycol and propylene glycol are each 0%, if the aqueous buffer solution contains one or more amino acids. Conversely, in these embodiments the total concentration of said one or more amino acids is 0 mM, if the aqueous buffer solution contains ethylene glycol or propylene glycol or both.

In some embodiments of the sixth aspect, the aqueous buffer solution comprises between 0% and 60% (v/v) (such as between 1% and 50% (v/v), between 5% and 40% (v/v), between 8% and 30% (v/v), between 10% and 25% (v/v), between 15% and 20% (v/v)) of ethylene glycol.

In those embodiments where the aqueous buffer solution contains at least one amino acid, the at least one amino acid is typically selected from the group consisting of alanine, asparagine, cysteine, glutamine, glycine, histidine, isoleucine, leucine, lysine, methionine, phenylalanine, proline, serine, threonine, and valine. In other words, in these embodiments aspartic acid, glutamic acid, tryptophan and tyrosine are absent. In those embodiments where the aqueous buffer solution contains at least one amino acid, the at least one amino acid is selected from the group consisting of alanine, cysteine, glycine, histidine, lysine, proline, serine, threonine, and valine. In other words, in these embodiments, asparagine, aspartic acid, glutamic acid, glutamine, isoleucine, leucine, methionine, phenylalanine, tryptophan and tyrosine are absent. In those embodiments where the aqueous buffer solution contains at least one amino acid, the at least one amino acid is typically selected from the group consisting of alanine, glycine, histidine, and lysine. In other words, in these embodiments, asparagine, aspartic acid, cysteine, glutamic acid, glutamine, isoleucine, leucine, methionine, phenylalanine, proline, serine, threonine, tryptophan, tyrosine and valine are typically absent.

In one embodiment of the sixth aspect, the at least one Good's buffer is selected from the group consisting of MES, MOPS, Tris, ADA, ACES, BES, Bicine, CAPS, CAPSO, CHES, HEPES, PIPES, TAPS, and TES. In one embodiment, the at least one Good's buffer is MES. In another embodiment, the at least one Good's buffer is MOPS.

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used but some experimental errors and deviations should be accounted for.

Example 1: Desorption of a Biomolecule Using a Combination of a Good's Buffer and an Amino Acid In this experiment, a biomolecule, agalsidase beta (Fabrazyme® manufactured by Genzyme, Cambridge, Mass.), was bound on multimodal chromatographic resin Capto™ Adhere (GE Healthcare) and desorbed using MES and MOPS (see Table 1 and FIGS. 1 and 2). The table shows the detailed experimental design, where a range of MES concentrations from 50 mM to 200 mM and MOPS concentrations from 20 mM to 200 mM was tested in the presence of 150 mM to 400 mM arginine within a pH range of 5.5 to 7.5. Yield was monitored in these experiments as an indicator of desorption from the chromatographic resin. Under a given buffer condition, 0% yield means no desorption and 100% means complete desorption of the biomolecule. The experimental design and analysis was done using Design-Expert®.

TABLE 1

Experimental design and results for elution with MES and MOPS

| MES (mM) | Arginine (mM) | pH | Yield (%) | MOPS (mM) | Arginine (mM) | pH | Yield (%) |
|---|---|---|---|---|---|---|---|
| 200 | 400 | 7 | 99 | 20 | 400 | 7.5 | 61 |
| 50 | 400 | 5.5 | 82 | 20 | 150 | 6.5 | 0 |
| 200 | 150 | 7 | 68 | 200 | 400 | 7.5 | 78 |
| 200 | 150 | 5.5 | 55 | 200 | 150 | 6.5 | 23 |
| 50 | 400 | 7 | 80 | 20 | 400 | 6.5 | 74 |
| 50 | 150 | 5.5 | 16 | 20 | 150 | 7.5 | 0 |
| 200 | 400 | 5.5 | 85 | 200 | 400 | 6.5 | 84 |
| 50 | 150 | 7 | 0 | 200 | 150 | 7.5 | 24 |

Figure 1:
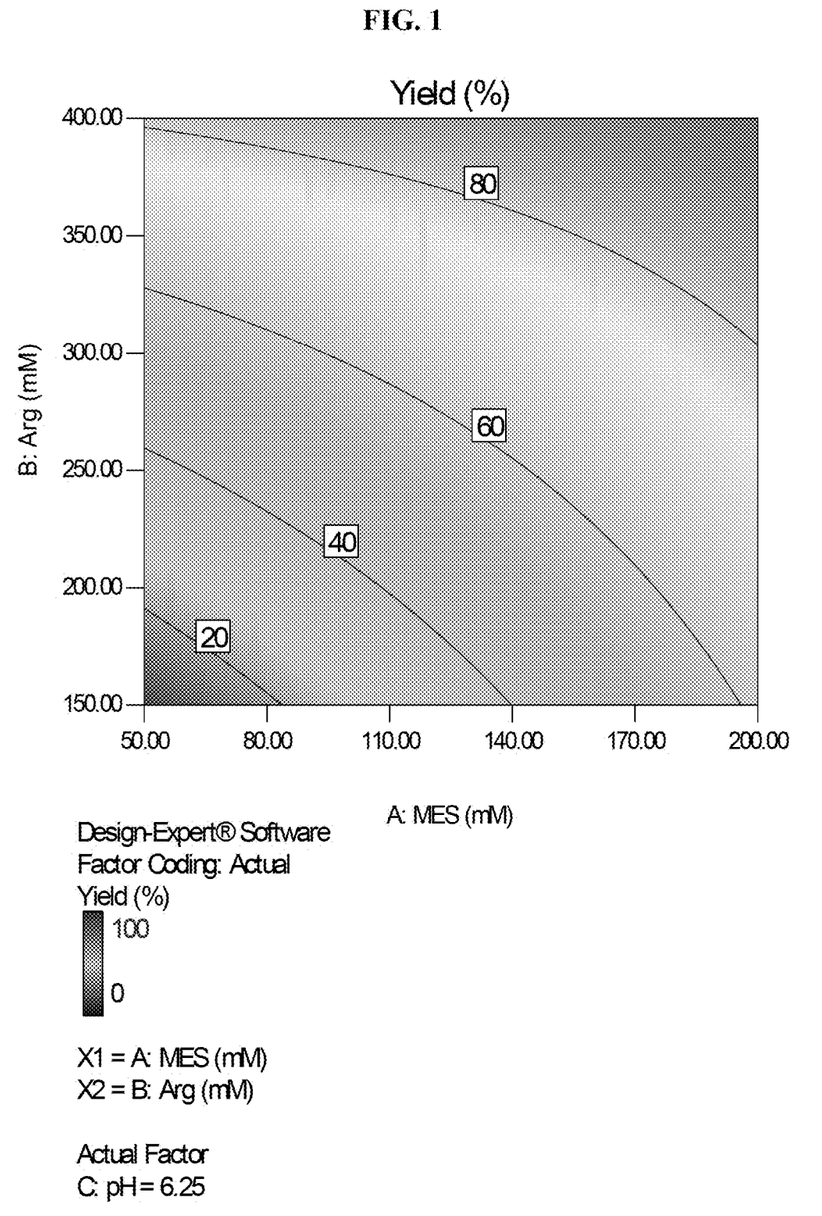
FIG. 1 is a contour plot for yield for an experiment in which agalsidase beta is desorbed from the multimodal chromatographic resin Capto™ Adhere (GE Healthcare) by an elution buffer containing MES and arginine. The contour plot is calculated for a pH value of 6.25.
Figure 2:
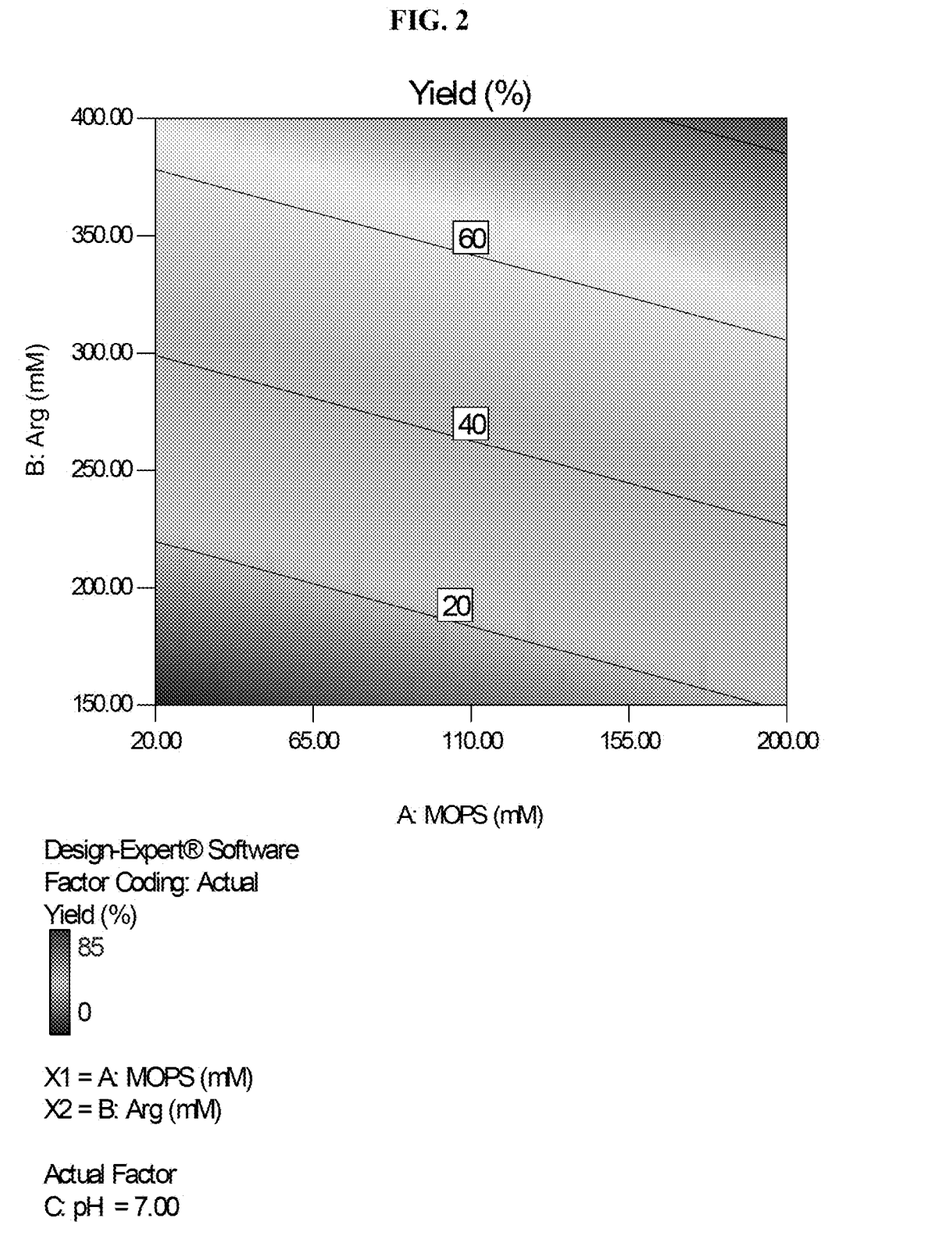
FIG. 2 is a contour plot for yield for an experiment in which agalsidase beta is desorbed from the multimodal chromatographic resin Capto™ Adhere (GE Healthcare) by an elution buffer containing MOPS and arginine. The contour plot is calculated for a pH value of 7.0.

FIG. 1 and FIG. 2 show contour plots for yield with MES at pH 6.25 and MOPS at pH 7.0, respectively. As expected from literature, for a given pH and concentration of MES, yield increases monotonically with increasing Arginine concentration. Surprisingly, for a given pH and Arginine concentration, yield increases monotonically with MES and MOPS concentration as well. Quantitatively, MES was found to be at least as effective as arginine in desorption, whereas, MOPS was slightly less effective than arginine. In summary, both MES and MOPS act similar to additives like arginine in desorbing the biomolecule from the multimodal resin.

MES and MOPS are considered to be particularly suitable additives for elution of biomolecules in downstream processing. This is because (i) MES and MOPS solutions are of lower conductivity than arginine and guanidine, allowing easier processing on a following ion exchange step; and (ii) solutions containing MES and MOPS are expected to be less disruptive for biomolecules than other additives, because biomolecular solutions of MES and MOPS are regularly used in biochemistry as part of Good's buffer systems.

Just like other additives (such as NaCl, urea, guanidinium salts etc.) can be applied to many different multimodal chromatographic resins, MES and MOPS can be used in desorption of biomolecules from other multimodal chromatographic resins available, such as Pall PPA HyperCel™, Pall HEA HyperCel™, Pall MEP HyperCel™ Capto™ MMC, and potentially various others multimodal resins which combine hydrophobic, ionic and/or hydrogen bonding interactions.

Furthermore, it is expected that other Good's buffers (e.g., ADA, ACES, BES, Bicine, CAPS, CAPSO, CHES, HEPES, MES, MOPS, PIPES, TAPS, TES, and Tris) exhibit similar advantageous properties as MES and MOPS in the desorption of biomolecules from multimodal chromatographic resins.

Figure 3:
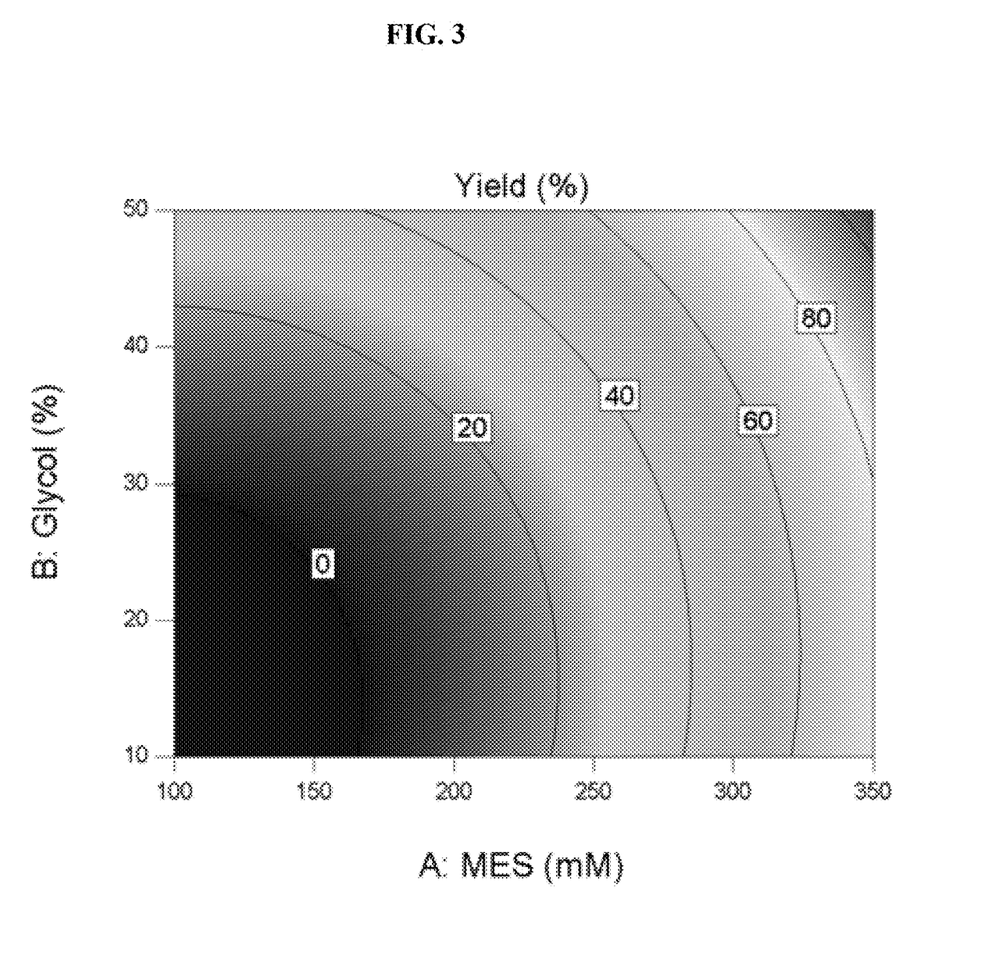
FIG. 3 is a contour plot for yield for an experiment in which agalsidase beta is desorbed from the multimodal chromatographic resin Capto™ Adhere (GE Healthcare) by an elution buffer containing MES and glycol.

Example 2: Desorption of a Biomolecule Using a Combination of a Good's Buffer and Glycol The experiment from Example 1 was modified in that arginine was replaced by ethylene glycol. The contour plot of this experiment is shown in FIG. 3.

TABLE 2

Experimental design and results for elution with MES and glycol

| MES (mM) | Glycol (% v/v) | Yield (%) |
|---|---|---|
| 225 | 58 | 95 |
| 402 | 30 | 108* |
| 100 | 10 | 0 |
| 225 | 30 | 29 |
| 225 | 30 | 14 |
| 225 | 2 | 2 |
| 350 | 50 | 95 |
| 225 | 30 | 13 |
| 350 | 10 | 96 |
| 225 | 30 | 23 |
| 48 | 30 | 10 |
| 100 | 50 | 14 |
| 225 | 30 | 33 |

*more than 100% yield is not possible and is only a result of measurement errors. It is, however, expected to be close to 100%.

Other embodiments are in the claims.

The invention claimed is:

1. A method for purifying or enriching an alpha-galactosidase, the method comprising:
 (a) providing an aqueous solution containing the alpha-galactosidase;
 (b) contacting the aqueous solution with a multimodal resin comprising immobilized N-benzyl-N-methylethanolamine;

(c) optionally, washing the multimodal resin with an aqueous washing buffer;
(d) eluting the alpha-galactosidase from the multimodal resin using an aqueous buffer solution, wherein the aqueous buffer solution comprises:
  (i) between 100 mM and 1.25 M of MES;
  (ii) between 25 mM and 300 mM arginine; and
  (iii) between 8% (v/v) and 30% (v/v) of ethylene glycol or propylene glycol or a mixture of ethylene glycol and propylene glycol;
and
(e) collecting alpha-galactosidase-containing fractions, thereby obtaining the alpha-galactosidase in purified or enriched form.

2. The method of claim 1, wherein the aqueous buffer solution comprises between 200 mM and 1.0 M MES.

3. The method of claim 1, wherein the aqueous buffer solution comprises between 50 mM and 250 mM arginine.

4. The method of claim 1, wherein the aqueous buffer solution comprises between 8% (v/v) and 30% (v/v) of ethylene glycol.

5. The method of claim 4, wherein the aqueous buffer solution comprises between 10% (v/v) and 25% (v/v) of ethylene glycol.

6. The method of claim 1, wherein the aqueous buffer solution has a pH of 5.5 to 7.5.

7. The method of claim 1, wherein the alpha-galactosidase is agalsidase beta.

8. A method for desorbing or increasing recovery rate of an alpha-galactosidase bound to a multimodal resin comprising immobilized N-benzyl-N-methyl-ethanolamine, wherein the method comprises contacting the alpha-galactosidase bound to the multimodal resin with an aqueous buffer solution comprising:
  (i) between 100 mM and 1.25 M of MES;
  (ii) between 25 mM and 300 mM arginine; and
  (iii) between 8% (v/v) and 30% (v/v) of ethylene glycol or propylene glycol or a mixture of ethylene glycol and propylene glycol.

9. The method of claim 8, wherein the aqueous buffer solution comprises between 200 mM and 1.0 M MES.

10. The method of claim 8, wherein the aqueous buffer solution comprises between 50 mM and 250 mM arginine.

11. The method of claim 8, wherein the aqueous buffer solution comprises between 8% (v/v) and 30% (v/v) of ethylene glycol.

12. The method of claim 11, wherein the aqueous buffer solution comprises between 10% (v/v) and 25% (v/v) of ethylene glycol.

13. The method of claim 8, wherein the aqueous buffer solution has a pH of 5.5 to 7.5.

14. The method of claim 8, wherein the alpha-galactosidase is agalsidase beta.

* * * * *